US00PP24422P3

(12) United States Plant Patent
Freyre

(10) Patent No.: US PP24,422 P3
(45) Date of Patent: May 6, 2014

(54) ***RUELLIA* PLANT NAMED 'R10-102'**

(50) Latin Name: *Ruellia simplex*
Varietal Denomination: R10-102

(75) Inventor: Rosanna Freyre, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 88 days.

(21) Appl. No.: 13/507,163

(22) Filed: Jun. 8, 2012

(65) Prior Publication Data

US 2013/0333084 P1 Dec. 12, 2013

(51) Int. Cl.
*A01H 5/00* (2006.01)

(52) U.S. Cl.
USPC ..... Plt./226; Plt./263.1

(58) Field of Classification Search
USPC ..... Plt./263.1, 226
See application file for complete search history.

(56) References Cited

U.S. PATENT DOCUMENTS

PP10,841 P 3/1999 Grant et al.

OTHER PUBLICATIONS

Freyre et al., "Breeding and evaluating for landscape performance and fruitlessness in Mexican petunia (*Ruellia,* Acanthaceae)," *HortScience,* 47:1245-1251, 2012.

*Primary Examiner* — Susan McCormick Ewoldt
(74) *Attorney, Agent, or Firm* — Dentons US LLP

(57) ABSTRACT

'R10-102' is a new *Ruellia* plant distinguished by having excellent landscape performance, violet flowers, and no fruiting, as disclosed.

2 Drawing Sheets

STATEMENT REGARDING FEDERALLY SPONSORED RESEARCH

The U.S. government has certain rights in this invention, pursuant to TSTAR Grant No. 00093296 awarded by the U.S. Department of Agriculture.

BACKGROUND OF THE INVENTION

Latin name of the genus and species of the plant claimed: *Ruellia simplex.*

Variety denomination: 'R10-102'.

The present invention relates to a new and distinct variety of *Ruellia*, botanically known as *Ruellia simplex*, and hereinafter referred to by the name 'R10-102.'

'R10-102' is a tetraploid individual which originated from a manual hybridization conducted in September 2010 in Gainesville, Fla. between UF breeding lines RU36 and 26-1. RU36 is a purple-flowering, tetraploid South American accession of *R. simplex.* 26-1 is a pink-flowering tetraploid breeding line, obtained as a vegetative propagule from RU3-26, which is a diploid-tetraploid chimeric individual obtained by treating the apical meristem of a seedling of *R. simplex* 'Chi Chi' with three applications (every 12 hours) of a 50 μM oryzalin solution in December 2008.

'R10-102' has been reproduced asexually for over one year through vegetative cuttings and has been shown to retain its distinctive characteristics through successive asexual propagations. The first asexual propagation of 'R10-102' was done by tip cuttings at the University of Florida Environmental Horticulture Research Greenhouses, Gainesville, Fla. 32611 in April 2011.

'R10-102' has not been made publicly available more than one year prior to the filing date of this application.

BRIEF SUMMARY OF THE INVENTION

The following are the most outstanding and distinguishing characteristics of 'R10-102' when grown under normal horticultural practices in Northwestern, North Central, and Southeastern Florida, USA:

1. Excellent performance in both full sun and partial shade environments.
2. Prolific flowering throughout the flowering season.
3. Large violet flowers.
4. No fruit production.

BRIEF DESCRIPTION OF THE DRAWINGS

The accompanying photographs illustrate the form and foliage of the new *Ruellia* variety. The colors shown are as true as can be reasonably obtained by conventional photographic procedures.

DETAILED BOTANICAL DESCRIPTION

Figure 1:
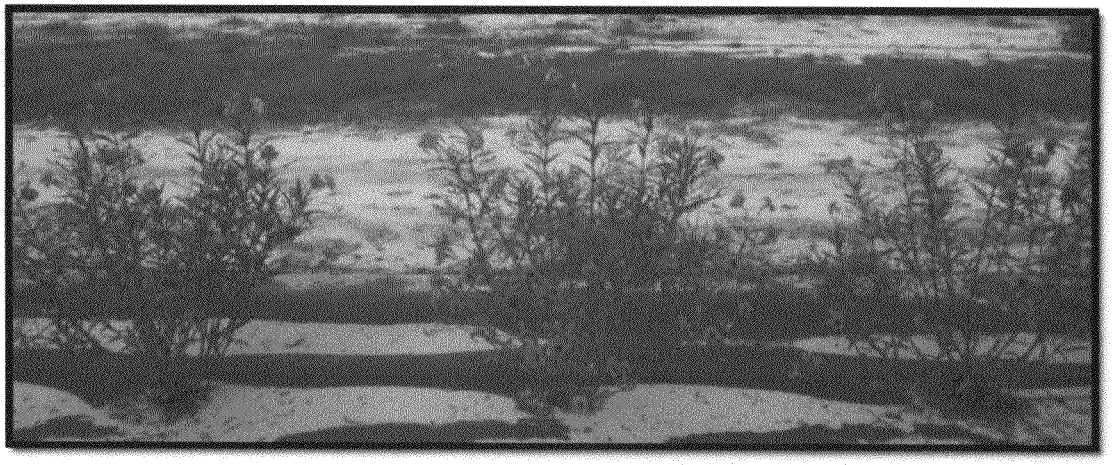
FIG. 1. Shows a plot of three plants of 'R10-102' taken on Aug. 29, 2011. The photograph was taken of 21-week-old plants grown in ground beds with drip irrigation at the Plant Science Research and Education Unit (PSREU) in Citra, Fla. (North Central Florida, 29.4° N., 82.2° W., AHS heat zone 10).
Figure 2:
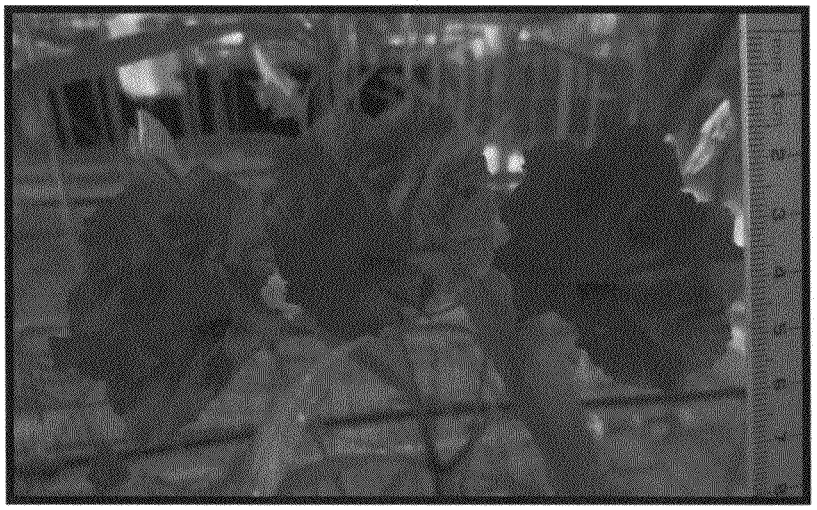
FIG. 2. Shows a close-up view of flowers of 'R10-102' on an 8-week-old greenhouse plant, taken on May 8, 2012.

The following detailed description sets forth the distinctive characteristics of 'R10-102.' The detailed description was taken on May 8, 2012, 8 weeks after vegetative propagation from greenhouse-grown stock plants. Measurements are the mean values from 3 individual clones propagated on Mar. 12, 2012 and greenhouse-grown in 6" Azalea pots using Fafard 2P mix (Concord Fafard Inc., Agawam, Mass.; 60% Canadian peat moss, 40% perlite) and fertigation at 150 ppm N.

Color references are to The R.H.S. Colour Chart of The Royal Horticultural Society of London (R.H.S.), 2001 Edition.

Phenotypic Description of *Ruellia simplex* (Variety 'R10-102')

Classification:

*Family*.—Acanthaceae.

*Botanical*.—*Ruellia simplex* hybrid.

*Common name*.—*Ruellia*, Mexican Petunia.

*Variety name*.—'R10-102'.

*Plant description*.—Form: Erect. Habit: Clumping. Height (from top of soil): 71.6 cm. Width (horizontal plant diameter): 54.6 cm.

Propagation:

*Type cuttings*.—Vegetative meristems having at least 2 nodes.

*Time to initiate roots*.—4 to 6 days.

*Time to produce a rooted cutting*.—7 to 10 days.

*Root habit*.—Adventitious (fibrous). Root description: Callus forms in 3 to 4 days; roots initiate in 5 to 8 days and become a highly branched cutting in 14 to 21 days.

Branches:

*Quantity per plant*.—5 to 7 per plant (with no pinching).

*Branch color*.—RHS 143A (Green).

*Texture*.—Smooth.

*Pubescence*.—Slightly tomentose, especially at nodes.

*Stem description*.—Round to square-shaped stem, 4.8 cm in diameter at the soil line.

*Branch diameter*.—2.6 cm at the base of a 32-cm long branch.

*Branch length*.—32.0 cm.

*Internode length*.—9.6 cm.

*Anthocyanin*.—RHS 183B (Grey/Purple).

Leaves:

*Quantity of leaves per branch*.—8 to 10.

*Arrangement*.—Decussate (opposite pairs).

*Fragrance*.—N/A.

*Shape*.—Lanceolate to elliptic.

*Length*.—22.6 cm.

*Width*.—3.7 cm.

*Apex*.—Narrowly Acute.

*Base*.—Attenuate.

*Margin*.—Entire.

*Leaf texture* (*both surfaces*).—Slightly coriaceous.

*Pubescence color* (*both surfaces*).—N/A.

*Venation color*.—Upper surface: RHS 139A (Green). Lower surface: RHS 137C (Green).

*Venation pattern*.—Pinnate.

*Color, mature and immature leaf*.—Upper surface: RHS 139A (Green). Lower surface: RHS 137C (Green).

*Petiole length*.—1.8 cm to 2.0 cm.

*Petiole diameter*.—0.4 cm.

*Petiole color*.—RHS 143A (Green).

Flowers and seeds:

*Flower* (*if present*).—Arrangement: Axillary in solitary or several-flowered cyme. Aspect: Actinomorphic corolla with 5 rounded petals; funnel form. Flowering habit (length of flowering season): May to October (N. FL). Number of inflorescences per plant: 6-10 cymes with 40-65 flowers+buds total Fragrance: Very mild and slightly sweet. Lastingness of individual bloom: 1 day. Rate of opening: Daily. Flower Bud: Shape: Elliptic. Length: 2.0 cm. Diameter: 1.2 cm. Color: RHS 143A (Green). Texture: Glandular with trichomes. Corolla: Arrangement: Actinomorphic salverform (funnel form) Length: 6.5 to 7.5 cm Diameter: 5.4 to 6.7 cm Color: Upper surface: RHS 87A (Violet) Lower surface: RHS 87A (Violet) Corolla tube: RHS 86B (Darker Violet) Banner: Not present Margin: Texture (both surfaces): Undulated Color: Upper surface: RHS 87A (Violet) Lower surface: RHS 87A (Violet) Keel: Not present Calyx: Number of sepals per flower: 5 Length: 2.0 cm Diameter: 1.5 cm Apex: Narrowly Acute Base: Fused Texture (both surfaces): Smooth to glandular (see below) Pubescence (present or absent): Present (Glandular trichomes) Sepal color: Upper surface: RHS 143A (Green) Lower surface: RHS 143A (Green) Pedicels: Angle: 15-25° Length: 0.8 cm Diameter: 0.7 cm Texture: Smooth to glandular Color: RHS 143A (Green). Reproductive organs: Stamens: Present. Number: 4 anthers with stamens fused at base to corolla. Filament: 4 (fused). Color: RHS 155D (White). Length: 2 at 2.0 cm, and 2 at 1.3 cm. Diameter: 0.2 cm. Anther color: N/A. Pollen amount: Moderate; 9% stainable, 4% appears to be 2n. Pollen color: RHS 155D (White). Pistils: Number/flower: 1. Pistil length: 3.2 cm. Stigma: Present. Color: RHS 155D (White). Shape: Bilabial and slightly recurved. Length: 0.2 cm. Diameter: 0.2 cm. Style: Color: RHS 155D (White). Length: 3 cm. Diameter: 0.2 cm. Ovary: Hypogenous. Shape: Elliptic. Color: RHS 143A (Green).

Fruit/seed set: None observed.

Disease and insect resistance: Disease and insect resistance is typical of the species.

Comparison with Parental Lines and Known Variety

Compared to the female parent RU36, 'R10-102' has a more compact and full growth habit, less rounded leaves, and no fruiting. Compared to the male parent 26-1, 'R10-102' is taller, with more elliptical leaves, violet flowers rather than pink flowers, and no fruiting.

Compared to *Ruellia simplex* 'Purple Showers' in North, Central, and Southeastern FL, 'R10-102' has an average height of 96 cm and width of 100 cm, as compared to 101 cm and 92 cm. The average landscape performance rating values (evaluated monthly from weeks 0 to 24 at three sites, based on a total of 27 plants) were 4.3 and 3.4 for 'R10-102' and 'Purple Showers,' respectively, where landscape performance was rated on a scale from 1-5, with 1 being very poor quality, not acceptable, severe leaf necrosis or chlorosis, and poor form; 2 being poor quality, not acceptable, large areas of necrosis or chlorosis, and poor form; 3 being acceptable quality, and somewhat desirable form and color; 4 being very good quality, very acceptable, and desirable color and form; and 5 being excellent quality, perfect condition, and premium color and form.

What is claimed is:

1. A new and distinct variety of *Ruellia* plant as shown and described herein.

* * * * *